United States Patent [19]

Okorodudu

[11] 4,405,470
[45] Sep. 20, 1983

[54] PHOSPHORODITHIOATE PRODUCTS OF HYDROCARBYL IMINO-METHYLENE-SUBSTITUTED HINDERED PHENOLS

[75] Inventor: Abraham O. M. Okorodudu, West Deptford, N.J.

[73] Assignee: Mobil Oil Corporation, New York, N.Y.

[21] Appl. No.: 341,718

[22] Filed: Jan. 22, 1982

[51] Int. Cl.³ .............................................. C10M 1/48
[52] U.S. Cl. .............................. 252/32.7 E; 252/46.6; 252/46.7; 252/400 A; 252/402; 260/944; 260/953
[58] Field of Search ............................... 260/944, 953; 252/32.7 E, 46.6, 46.7, 400, 402

[56] References Cited

U.S. PATENT DOCUMENTS 3,644,206  2/1972  Braid .................................. 252/46.7
3,812,220  5/1974  Robin et al. ....................... 260/953

Primary Examiner—Jacqueline V. Howard
Attorney, Agent, or Firm—Charles A. Huggett; Michael M. Gilman; Claude E. Setliff

[57] ABSTRACT

Product made by reacting a hindered phenol aldehyde with a primary amine followed by reacting the product thus obtained with a diorganophosphorodithioic acid, and lubricants containing same.

18 Claims, No Drawings

PHOSPHORODITHIOATE PRODUCTS OF HYDROCARBYL IMINO-METHYLENE-SUBSTITUTED HINDERED PHENOLS

BACKGROUND OF THE INVENTION

1. Field of the Invention:

The invention relates to products made by reacting a hindered phenol aldehyde with a nitrogen-containing compound, followed by reaction with a phosphorodithioic acid and to lubricant compositions containing same. More particularly, the product is made by reacting the aldehyde with a primary amine, followed by reaction thereof with a diorganophosphorodithioic acid.

2. Discussion of the Prior Art:

Many industrial organic media are used under circumstances which contribute to their breakdown during service. Such media include lubricants and greases, hydraulic fluids for brake and transmission systems, resins and plastics for coatings and structural articles. The severe operating conditions of modern engines, for example, including automotive and gas turbine engines, have often caused lubricating oils to deteriorate rapidly during use. This oxidation deterioration is accelerated by the use of higher engine operating temperatures than formerly used. Oxidative deterioration of the oil is usually accompanied by the formation of gummy deposits, sludge, acids, which may be strong enough to cause metal corrosion and other products of chemical breakdown. The products may seriously interfere with the lubrication operation. The increase in viscosity, for example, which results from the oxidation of lubricants, impairs the proper function of engine components and depreciates engine performance and useful life.

Organic media therefore may be blended with certain additives, termed "antioxidants" to protect against oxidation. Although many of the older known additives have been found to be adequate in stabilizing some modern mineral oil lubricants and synthetic lubricant blends, discovery of the new and more effective additives would be highly desirable for improved protection in current engines and extension of operating limits for future engines.

U.S. Pat. No. 3,644,172 discloses a product made by reacting a diorgano dithiophosphoric acid ester with a vinyl carboxylate. The product is useful as an antioxidant in lubricants.

U.S. Pat. No. 3,644,206 teaches a product useful as an antioxidant in an organic fluid. The product is made by reacting a diorganodithiophosphoric acid with a cyclic hindered aldehyde. The acid ester and the aldehyde react together in a 1:1 ratio.

It is one object of this invention to provide novel organic compositions which have improved oxidation stability and antiwear activity. It is a further object of this invention to provide novel compositions which afford protection against oxidation deterioration for organic media to which they have been added. Another object is to provide improved lubricating oil compositions capable of withstanding the oxidizing conditions of modern engines. These and other objects will become apparent from the following disclosure.

SUMMARY OF THE INVENTION

In accordance with the invention, there is provided a product of the formula

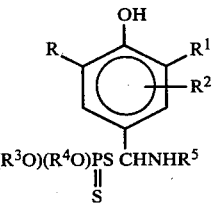

wherein R, $R^1$, $R^2$, $R^3$, $R^4$ and $R^5$ are hydrocarbyl groups containing 1 to 30 carbon atoms. Preferably, R and $R^1$ are the same or different $C_3$–$C_{20}$ alkyl groups in any isomeric arrangement provided that the carbon atom attached to the ring is attached to at least two other carbon atoms, $R^2$ is hydrogen or a $C_1$–$C_{20}$ alkyl, aryl, aralkyl or alkaryl group, preferably hydrogen, $R^3$ and $R^4$ are the same or different $C_1$–$C_{20}$ alkyl or the same or different $C_6$–$C_{30}$ alkenyl or alkyl group or a $C_6$–$C_{30}$ cycloalkyl, substituted cycloalkyl, aryl, aralkyl or alkaryl group.

The invention also provides a lubricant composition comprising a major proportion of a lubricant and an anticorrosion or antiwear proportion of said product.

DESCRIPTION OF SPECIFIC EMBODIMENTS

The product is prepared by reacting a free hindered phenol aldehyde with a primary amine, followed by reaction with a phosphorodithioic acid, as follows:

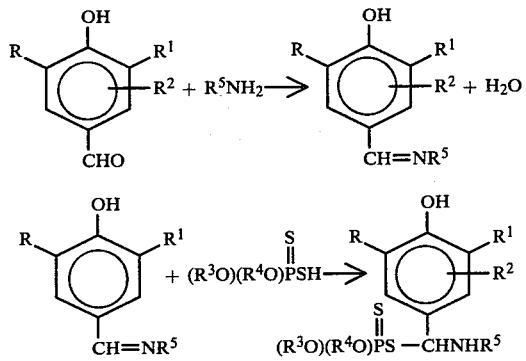

Equimolar amounts of the hindered phenol aldehyde and the primary amine are heated in a suitable solvent, e.g., toluene or benzene, to reflux under slight $N_2$ purge until the theoretical amount of water is collected in a Dean-Stark trap. An equimolar amount of phosphorodithioic acid is then added at a lower temperature and the reaction mixture is again brought to reflux and kept there until completion of the reaction as indicated by the IR of the product mixture. After cooling, the reaction mixture is diluted with toluene, washed with 10% $Na_2CO_3$, dried over anhydrous $MgSO_4$ and stripped of solvent to give the product.

The hindered phenol aldehydes may be purchased or they can be prepared by the bromine oxidation, in t-butyl alcohol, of, for example, di-t-butyl-p-cresol or m,m-di-t-butyl-p-hydroxy-benzyl alcohol. See J. Am. Chem. Soc, 75, 734 (1953). Included among the useful aldehydes are 3,5-di-isopropyl-4-hydroxybenzaldehyde and 3,5-di-t-octyl-4-hydroxybenzaldehyde.

The phosphorodithioic acids can be made easily by the prior art method of reacting the appropriate alcohol with phosphorus pentasulfide, in accordance with the reaction

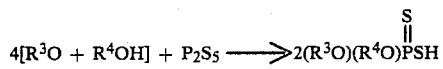

Any well known alcohol or mixture of alcohols which satisfies the definition of $R^3$ and $R^4$ would suffice.

The appropriate primary amines include both aliphatic and aromatic primary amines. The aliphatic amines are preferably fatty amines having 3 to 18 carbon atoms and the aromatic amines or the ring-substituted members thereof. The preferred amines include 2-ethylhexylamine, dodecylamine, octadecylamine, oleylamine, aniline, ring-substituted anilines, e.g., p-t-butylaniline, dodecylaniline and dimethoxyaniline, etc.

In general, the product is employed in an antioxidant or antiwear amount and particularly from about 0.05% to about 10% by weight, and preferably from about 0.25% to about 2% by weight of the total weight of the composition.

Of particular significance, is the ability to counteract the accelerating effect of oxidation on metal and lubricant deterioration achieved by employing the aforementioned product. These products may be incorporated in lubricating media which may comprise liquid hydrocarbon oils in the form of either a mineral oil or a synthetic oil, or in the form of a grease, in which any of the aforementioned oils are employed as a vehicle. In general, mineral oils employed as the lubricant or grease vehicle may be of any suitable lubricating viscosity range as, for example, from about 45 SSU at 100° F. to about 6,000 SSU at 100° F., and preferably from about 50 SSU at 210° F. to about 250 SSU at 210° F. These oils may have viscosity indexes varying from below 0 to about 100 or higher. Viscosity indexes from about 70 to about 95 are preferred. The average molecular weights of these oils may range from about 250 to 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, di(-butylphthalate) fluorocarbons, silicate esters, silanes, esters of phosphorous-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis(p-phenoxy phenyl)ether, phenoxy phenylethers, etc.

The lubricating vehicles of the aforementioned greases of the present invention, containing the above-described products, are combined with a grease-forming quantity of a thickening agent. For this purpose, a wide variety of materials may be employed. These thickening or gelling agents may include any of the conventional metal salts or soaps, which are dispersed in the lubricating vehicle in grease-forming quantities, in such degree as to impart to the resulting grease composition the desired consistency. Other thickening agents that may be employed in the grease formation may comprise the non-soap thickeners, such as surface modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for forming greases, can be used in preparing the aforementioned improved greases in accordance with the present invention.

The following Examples will specifically illustrate the invention. It will be understood that they are meant to be illustrations of and not limitations to the invention.

EXAMPLE 1

Octadecylamine, 54 g (0.2 moles), 3,5-di-t-butyl-4-hydroxybenzaldehyde, 47 g (0.2 moles), and 150 ml of toluene were charged into a 1 liter reaction flash equipped with a Dean-Stark trap. The mixture was heated slowly to reflux under a mild $N_2$ purge. After the theoretical amount of water was collected, the heat was turned off and the reaction mixture allowed to cool. 1R of the reaction mixture showed no carbonyl absorption. 0,0'-di-4-methyl-2-pentyl phosphorodithioic acid, 60 g (0.2 moles) was added rapidly to the above mixture at ambient temperature. Following a mild exothermic reaction, the reaction mixture was heated at 80° C. for 7 hours under mild $N_2$ blanket, cooled, diluted with toluene, and washed with 10% $Na_2CO_3$. After drying over anhydrous $MgSO_4$, the organic portion was stripped to give a viscous dark brown liquid.

EXAMPLE 2

This compound was prepared according to the above procedure, using 53 g (0.2 moles) of oleylamine, 47 g (0.2 moles) of 3,5-di-t-butyl-4-hydroxybenzaldehyde, 150 ml of toluene and 60 g (0.2 moles) of 0,0'-di-4-methyl-2-pentyl phosphorodithioic acid.

EXAMPLE 3

Prepared as in Example 1, using 52 g (0.2 moles) of dodecylaniline, 47 g (0.2 moles) of 3,5-di-t-butyl-4-hydroxybenzaldehyde, 150 ml of toluene and 60 g (0.2 moles) of 0,0'-di-4-methyl-2-pentyl phosphorodithioic acid.

EXAMPLE 4

Prepared according to the procedure of Example 1, using 37 g (0.2 moles) of dodecylamine, 47 g (0.2 moles) of 3,5-di-t-butyl-4-hydroxybenzaldehyde, 150 ml of toluene and 60 g (0.2 moles) of 0,0'-di-4-methyl-2-pentyl phosphorodithioic acid.

EVALUATION OF PRODUCTS

Oxidation Test

The products were evaluated for oxidation stability. In most cases, improvements in oxidative stability over the base oil were observed. Basically, in this test, the lubricant is subjected to a stream of air which is bubbled through at the rate of about 5 liters per hour at 325° F. for 40 hours. Present in the composition are samples of metals commonly used in engine construction, namely iron, copper, aluminum and lead. See U.S. Pat. No.

3,682,980, incorporated herein by reference, for further details of the test. Improvement in viscosity index or neutralization number (or both) show effective control. See the results in Table 1. The oil used was a 130" solvent paraffinic neutral mineral oil.

TABLE 1

CATALYTIC OXIDATION TEST

| Additive | Conc. Wt. % | NN Initial | NN Final | Viscosity, KV, cS@ 100° F. Initial | Viscosity, KV, cS@ 100° F. Final | Oxidized Oil NN | Oxidized Oil KV % | Oxidized Oil Pb. Loss mg | Oxidized Oil Sludge |
|---|---|---|---|---|---|---|---|---|---|
| None | — | — | — | — | — | 17.8 | 202 | 171.3 | Light |
|  | — | — | — | — | — | 17.0 | 334 | 66.0 | Heavy |
| Example 1 | 2 | 1.46 | 0.80 | 4.916 | 5.179 | −0.66 | 5 | 0 | Heavy |
|  | 1 | 0.73 | 1.48 |  | 5.254 | 0.75 | 7 | 0 | Heavy |
|  | 0.5 | 0.37 | 4.61 |  | 5.882 | 4.24 | 20 | 0 | Heavy |
|  | 0.25 | 0.18 | 7.50 |  | 6.650 | 7.32 | 35 | 0 | Heavy |
| Example 2 | 2 | 1.05 | 0.41 | 4.900 | 5.121 | −0.64 | 5 | 0 | Heavy |
|  | 1 |  | 1.11 |  | 5.284 | 0.59 | 8 | 0 | Heavy |
|  | 0.5 |  | 3.63 |  | 5.689 | 3.37 | 16 | 0 | Heavy |
|  | 0.25 |  | 4.25 |  | 5.678 | 4.12 | 16 | 1 | Heavy |
| Example 3 | 2 | 0.84 | 0.60 | 4.879 | 5.217 | −0.24 | 7 | 0 | Trace |
|  | 1 |  | — |  | 5.115 | — | 5 | 0 | Heavy |
|  | 0.5 |  | 3.15 |  | 5.587 | 2.94 | 15 | 0 | Heavy |
|  | 0.25 |  | 3.53 |  | 5.793 | 3.43 | 19 | 0 | Heavy |
| Example 4 | 2 | 1.53 | 0.53 | 4.913 | 5.193 | −1.0 | 6 | 0 | Heavy |
|  | 1 |  | 3.47 |  | 5.695 | 2.71 | 16 | 0 | Heavy |
|  | 0.5 |  | 3.90 |  | 5.483 | 3.52 | 12 | 1.2 | Heavy |
|  | 0.25 |  | 2.77 |  | 5.488 | 2.58 | 12 | 2.2 | Heavy |

SHELL 4-BALL WEAR TEST

The products were also tested in the Shell 4-Ball Wear Test, which tests for scarring. In the test, 52100 stainless steel balls were used under a 60 Kg load for 30 minutes. The oil used was a 80/20 mixture of 150" solvent paraffinic bright mineral oil and 200" solvent paraffinic neutral mineral oil. Results are in Table 2.

TABLE 2

| Additive | Conc. Wt. % | Temp. °F. | SCAR DIAMETER, mm 500 RPM | 1,000 RPM | 1,500 RPM | 2,000 RPM |
|---|---|---|---|---|---|---|
| Base Oil | 100 | Room | — | — | — | — |
|  |  | 200 | 0.50 | 1.40 | 2.1 | 1.4 |
|  |  | 390 | 0.70 | 1.60 | 2.4 | 2.0 |
| Example 1 | 1 | Room | 0.30 | 0.33 | 0.43 | 0.53 |
|  |  | 200 | 0.30 | 0.33 | 0.40 | 0.46 |
|  |  | 390 | 0.55 | 0.70 | 1.28 | 1.65 |
| Example 2 | 1 | Room | 0.40 | 0.50 | 0.60 | 0.70 |
|  |  | 200 | 0.40 | 0.43 | 0.53 | 0.70 |
|  |  | 390 | 0.75 | 0.80 | 1.20 | 1.60 |
| Example 3 | 1 | Room | 0.30 | 0.40 | 0.53 | 0.63 |
|  |  | 200 | 0.31 | 0.40 | 0.58 | 0.70 |
|  |  | 390 | 0.90 | 1.15 | 1.65 | 1.83 |
| Example 4 | 1 | Room | 0.40 | 0.55 | 0.70 | 1.41 |
|  |  | 200 | 0.40 | 0.47 | 0.63 | 0.70 |
|  |  | 390 | 0.55 | 0.70 | 0.80 | 1.65 |

We claim:

1. A compound of the formula

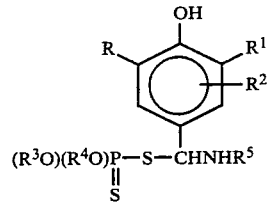

wherein R, $R^1$, $R^2$, $R^3$, $R^4$ and $R^5$ are hydrocarbyl groups containing from 1 to 30 carbon atoms.

2. The compound of claim 1 wherein R and $R^1$ are the same or different $C_3$–$C_{16}$ secondary alkyl groups, $R^2$ is hydrogen or a $C_1$–$C_{20}$ alkyl, aryl, aralkyl or alkaryl group, $R^3$ and $R^4$ are the same or different $C_1$–$C_{20}$ alkyl groups or the same or different $C_6$–$C_{30}$ aryl, aralykl or alkaryl groups and $R^5$ is a $C_1$–$C_{30}$ alkenyl or alkyl group, a $C_6$–$C_{30}$ cycloalkyl group or a substituted cycloalkyl, aryl, aralkyl or alkaryl group.

3. The compound of claim 1 wherein $R^2$ is hydrogen.

4. The compound of claim 1 wherein R and $R^1$ are tert-butyl groups, $R^2$ is hydrogen, $R^3$ and $R^4$ are 4-methyl-2-pentyl groups and $R^5$ is an octadecyl group.

5. The compound of claim 1 wherein R and $R^1$ are tert-butyl groups, $R^2$ is hydrogen, $R^3$ and $R^4$ are 4-methyl-2-pentyl groups and $R^5$ is an oleyl group.

6. The compound of claim 1 wherein R and $R^1$ are tert-butyl groups, $R^2$ is hydrogen, $R^3$ and $R^4$ are 4-methyl-2-pentyl groups and $R^5$ is a dodecylphenyl group.

7. The compound of claim 1 wherein R and $R^1$ are tert-butyl groups, $R^2$ is hydrogen, $R^3$ and $R^4$ are 4-methyl-2-pentyl groups and $R^5$ is a dodecyl group.

8. A lubricant composition comprising a major amount of a lubricant and a minor antioxidant or antiwear amount of a compound of the formula

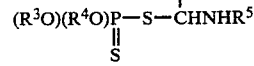

wherein R, $R^1$, $R^2$, $R^3$, $R^4$ and $R^5$ are hydrocarbyl groups containing 1 to 30 carbon atoms.

9. The composition of claim 8 wherein in the compound R and $R^1$ are the same or different $C_3$–$C_{16}$ secondary alkyl groups, $R^2$ is hydrogen or a $C_1$–$C_{20}$ alkyl, aryl, aralkyl or alkaryl group, $R^3$ and $R^4$ are the same or different $C_1$–$C_{20}$ alkyl groups or the same or different $C_6$–$C_{30}$ aryl, aralykl or alkaryl groups and $R^5$ is a $C_1$–$C_{30}$ alkenyl or alkyl group, a $C_6$–$C_{30}$ cycloalkyl group or a substituted cycloalkyl, aryl aralkyl or alkaryl group.

10. The composition of claim 8 wherein in the compound $R^2$ is hydrogen.

11. The composition of claim 1 wherein in the compound R and $R^1$ are tert-butyl groups, $R^2$ is hydrogen, $R^3$ and $R^4$ are 4-methyl-2-pentyl groups and $R^5$ is an octadecyl group.

12. The composition of claim 1 wherein in the compound R and $R^1$ are tert-butyl groups, $R^2$ is hydrogen, $R^3$ and $R^4$ are 4-methyl-2-pentyl groups and $R^5$ is an oleyl group.

13. The composition of claim 1 wherein in the compound R and $R^1$ are tert-butyl groups, $R^2$ is hydrogen, $R^3$ and $R^4$ are 4-methyl-2-pentyl groups and $R^5$ is dodecylphenyl dodecylanilino group.

14. The composition of claim 1 wherein in the compound R and $R^1$ are tert-butyl groups, $R^2$ is hydrogen, $R^3$ and $R^4$ are 4-methyl-2-pentyl groups and $R^5$ is a dodecyl group.

15. The composition of claims 8, 9, 10, 11, 12, 13 or 14 wherein said lubricant is (1) a mineral oil, (2) a synthetic oil, (3) a mixture of (1) or (2) or, (4) a grease from either of (1), (2) or (3).

16. The composition of claim 15 wherein the lubricant is a mineral oil.

17. The composition of claim 8 wherein the lubricant is a synthetic oil.

18. The composition of claim 8 wherein the lubricant is a grease.

* * * * *

UNITED STATES PATENT AND TRADEMARK OFFICE
CERTIFICATE OF CORRECTION

PATENT NO. : 4,405,470
DATED : September 20, 1983
INVENTOR(S) : Abraham O. M. Okorodudu It is certified that error appears in the above—identified patent and that said Letters Patent is hereby corrected as shown below:

Column 6, line 67, claim 9, after "aryl" insert --,--.

Column 7, line 15, claim 13, delete "dodecylanilino".

*Signed and Sealed this*

*Third* Day of *January 1984*

[SEAL]

*Attest:*

GERALD J. MOSSINGHOFF

*Attesting Officer*     *Commissioner of Patents and Trademarks*